(12) United States Patent
Hassibi et al.

(10) Patent No.: US 7,141,370 B2
(45) Date of Patent: Nov. 28, 2006

(54) BIOLUMINESCENCE REGENERATIVE CYCLE (BRC) FOR NUCLEIC ACID QUANTIFICATION

(75) Inventors: Arjang Hassibi, Palo Alto, CA (US); Nader Pourmand, San Carlos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/186,455

(22) Filed: Jun. 28, 2002

(65) Prior Publication Data

US 2003/0082583 A1 May 1, 2003

Related U.S. Application Data

(60) Provisional application No. 60/302,909, filed on Jul. 3, 2001.

(51) Int. Cl.
*C12Q 1/68* (2006.01)
*C12P 19/34* (2006.01)

(52) U.S. Cl. .......................................... 435/6; 435/91.2

(58) Field of Classification Search .................... 435/6, 435/91.1, 91.2; 536/23.1, 24.3, 24.31, 24.32, 536/24.33
See application file for complete search history.

(56) References Cited

U.S. PATENT DOCUMENTS

| | | | |
|---|---|---|---|
| 4,971,903 A | 11/1990 | Hyman | |
| 5,534,424 A | 7/1996 | Uhlen et al. | |
| 5,854,033 A * | 12/1998 | Lizardi ........................ | 435/91.2 |
| 6,197,505 B1 | 3/2001 | Norberg et al. | |
| 6,210,891 B1 | 4/2001 | Nyren et al. | |
| 6,255,083 B1 | 7/2001 | Williams | |
| 6,258,568 B1 | 7/2001 | Nyren | |
| 6,270,973 B1 | 8/2001 | Lewis et al. | |
| 6,274,320 B1 | 8/2001 | Rothberg et al. | |
| 6,534,269 B1 | 3/2003 | Liu et al. | |
| 2003/0087272 A1 | 5/2003 | Kambara et al. | |
| 2003/0219891 A1 | 11/2003 | Yazawa et al. | |

FOREIGN PATENT DOCUMENTS

| | | |
|---|---|---|
| CA | 2 440 698 A1 | 8/2002 |
| FR | 2 674 254 | 9/1992 |
| WO | WO 89/09283 | 5/1989 |
| WO | WO 93/23564 | 11/1993 |
| WO | WO 01/42496 | 6/2001 |
| WO | WO 02/20836 | 3/2002 |
| WO | WO 02/064830 A2 | 8/2002 |
| WO | WO 2004/062338 A2 | 7/2004 |

OTHER PUBLICATIONS

Nygre, M. et al., "Quantification of HIV-1 Using Multiple Quantitative Polymerase Chain reaction Standards and Bioluminometri Detection", Anal. Biochem, vol. 288, pp. 28-38 (Jan. 2001).*
Tabary, T. et al., "Homogeneous phase pyrophosphate (PPi) measurement (H3PIM)", J. Immunol. Meth., vol. 156, pp. 55-60 (1992).*
Schena, M. et al., "Parallel human genome analysis: Microarray-based expression monitoring of 1000 genes", PNAS, vol. 93, pp. 10614-10619 (1996).*
Larrick, J. W., "Message Amplification Phenotyping (MAPPing)—principles, practice and potential", Trends in Biotechnology, vo 10. pp. 146-152 (1992).*
Abravaya, K et al., "Performance of a Multiplex Qualitative PCR LCx Assay for Detection of Human Immunodeficiency Virus Type 1 (HIV-1), Group M Subtypes, Group O, and HIV-2", J. Clin. Microbiol., vol. 38, pp. 716-723 (Feb. 2000).*
Deardorff, D., "Measurement Uncertainty Instructional Resources", University of North Carolina at Chapel Hill Department of Physics Web page at www.physics.unc.edu/~deardorf/uncertainty, last revision Aug. 12, 2003.*
Ahmadian, et al., "Genotyping by Apyrase-Mediated Allele-Specific Extension," *Nucleic Acids Research*, 2001, vol. 29, No. 24.
Banér, et al., "Signal Amplification of Padlock Probes by Rolling Circle Replication," *Nucleic Acids Research*, 1998, vol. 26, No. 22, 5073-5078.
Beynon, et al., "Crystal Structure of ATP Sulfurylase from the Bacterial Symbiont of the Hydrothermal Vent Tubeworm *Riftia pachyptila*," Biochemistry 2001, 40, 14509-14517.

(Continued)

*Primary Examiner*—Teresa E. Strzelecka
(74) *Attorney, Agent, or Firm*—David J. Aston; Peters, Verny, Jones, Schmitt & Aston, LLP

(57) ABSTRACT

The present invention concerns methods of quantifying nucleic acids using a bioluminescence regenerative cycle (BRC). In BRC, steady state levels of bioluminescence result from processes that produce pyrophosphate. Pyrophosphate reacts with APS in the presence of ATP sulfurylase to produce ATP. The ATP reacts with luciferin in a luciferase-catalyzed reaction, producing light and regenerating pyrophosphate. The pyrophosphate is recycled to produce ATP and the regenerative cycle continues. Because the kinetic properties of ATP sulfurylase are much faster than luciferase, a steady state results wherein concentrations of ATP and pyrophosphate and the rate of light production remain relatively constant. Photons are counted over a time interval to determine the number of target molecules present in the initial sample. The BRC process has a controllable dynamic range up to seven orders of magnitude and is sensitive enough to detect a few thousand molecules of target nucleic acid.

6 Claims, 12 Drawing Sheets

OTHER PUBLICATIONS

Brenner, et al., "Gene Expression Analysis by Massively Parallel Signature Sequencing (MPSS) on Microbead Arrays," *Nature Biotechnology*, vol. 18, Jun. 2000, 630-634.

Brovko, "Kinetics of Bioluminescence in the Firefly Luciferin-Luciferase System," *Biochemistry (Moscow)*, vol. 59, No. 2, 1994.

Erlandsson, "Quantification of *Bordetella pertussis* in Clinical Samples by Colorimetric Detection of Competitive PCR Products," *APMIS* 106: 1041-1048, 1998.

Fakhrai-Rad, et al., "Pyrosequencing: An Accurate Detection Platform for Single Nucleotide Polymorphisms," *Human Mutation* 19:479-485, 2002.

Garcia, et al., "Mutation Detection by Pyrosequencing: Sequencing of Exons 5-8 fo the p53 Tumor Suppressor Gene," *Gene*, 253 (2000) 249-257.

Goergen, et al., "Mutation Specific PCR and Direct Solid Phase Sequencing Assay for the Detection of Hepatitis B Virus Pre-C/C Mutants in Anti-HBe-Positive, Chronic Hepatitis B," *Journal of Medical Virology* 43:97-102, 1994.

Higgins, et al., "Competitive Oligonucleotide Single-Base Extension Combined with Mass Spectrometric Detection for Mutation Screening," *BioTechniques* 23:710-714, Oct. 1997.

Karamohamed, et al., "Production, Purification, and Luminometric Analysis of Recombinant *Saccharomyces cerevisiae* MET3 Adenosine Triphosphaste Sulfurylase Expressed in *Escherichia coli,*" *Protein Expression and Purification*, 15, 381-388 (1999).

Karamohamed, et al., "Real-Time Bioluminometric Method for Detection of Nucleoside Diphosphate Kinase Activity," *BioTechniques* vol. 26, No. 4, Apr. 1999.

Karamohamed, et al., "Real-Time Detection and Quantification of Adenosine Triposphate Sulfurylase Activity by a Bioluminometric Approach," *Analytical Biochemistry*, 271, 81-85 (1999).

Khan, "Plasmid Rolling-Circle Replication: Recent Developments," *Molecular Microbiology* (2000) 37(3), 477-484.

Newton, "Analysis of any Point Mutation in DNA. The Amplification Refractory Mutation System (ARMS)," *Nucleic Acids Research*, vol. 17, No. 7, 1989, 2503-2516.

Nordström, "Method Enabling Fast Partial Sequencing of cDNA Clones," *Analytical Biochemistry* 292, 266-271 (2001).

Nygren, et al. "Quantification of HIV-1 Using Multiple Quantitative Polymerase Chain Reaction Standards and Bioluminometric Detection," *Analytical Biochemistry*, 288, 28-38 (2001).

Nyrén, "Enzymatic Method for Continuous Monitoring of DNA Polymerase Activity," *Analytical Biochemistry*, 167, 235-238 (1987).

Nyrén, et al., "Enzymatic Method for Continuous Monitoring of Inorganic Pyrophosphate Synthesis," *Analytical Biochemistry*, 151, 504-509 (1985).

Nyrén, et al., "Detection of Single-Base Changes Using a Bioluminometric Primer Extension Assay," *Analytical Biochemistry*, 244, 367-373 (1997).

Pourmand, et al., "Mutiplex Pyrosequencing," *Nucleic Acids Research*, 2002, vol. 30, No. 7 (2002).

Renosto, et al., "ATP Sulfurylase from Trophosome Tissue of *Riftia pachyptila* (Hydrothermal Vent Tube Worm)," *Archives of Biochemistry and Biophysics*, vol. 290, No. 1, Oct., pp. 66-78, 1991.

Ronaghi, et al., "Pyrosequencing Sheds Light on DNA Sequencing," Genome Research, 11:3-11, 2001.

Ronaghi, et al., "Real-Time DNA Sequencing Using Detection of Pyrophosphate Release," *Analytical Biochemistry* 242, 84-89 (1996).

Ronaghi, et al., "Real-Time Pyrophosphate Detection for DNA Sequencing," *Science*, vol. 281, 363-365, Jul. 1998.

Vener, et al., "Use of Multiple Competitors for Quantification of Human Immunodeficiency Virus Type I RNA in Plasma," *Journal of Clinical Microbiology*, Jul. 1998, p. 1864-1870.

Vu, et al., "A Method for Quantification of Absolute Amounts of Nucleic Acids by (RT)-PCR and a New Mathematical Model for Data Analysis," *Nucleic Acids Research*, 2000, vol. 28, No. 7.

Xu, et al., "A Bioluminescence Resonance Energy Transfer (BRET) System: Application to Interacting Circadian Clock Proteins," *Proc. Natl. Acad. Sci. USA*, vol. 96, pp. 151-156, Jan. 1999.

International Search Report PCT/US02/20690, Dec. 4, 2003.

Karamohamed et al., "Bioluminometric method for real-time detection of reverse transcriptase activity", Biotechniques, 24(2):302-306 (1998).

\* cited by examiner

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
cggcgataaa ggctataacg g                                          21

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
cggcgataaa ggctataacg g                                          21

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
ctggaacgct ttgtccgggg                                            20
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ctggaacgct ttgtccgggg                                                      20

<210> SEQ ID NO 5
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 5 ttttttttt ttttttttt gctggaattc gtcagactgg ccgtcgtttt acaacggaac            60
ggcagcaaaa tgttgc                                                          76
```

BIOLUMINESCENCE REGENERATIVE CYCLE (BRC) FOR NUCLEIC ACID QUANTIFICATION

The present application claims the benefit under 35 U.S.C. §119(e) of provisional Patent Application Serial No. 60/302,909, filed on Jul. 3, 2001, entitled "Gene Expression by Analyzing DNA Optical Extension Signature," by Hassibi and Pourmand.

The invention described herein was made with Government support under grant 5 P01 HG00205 from the National Institutes of Health. The Federal Government may have certain rights in the subject invention.

BACKGROUND OF THE INVENTION

1. Field of the Invention

The present invention relates to the field of nucleic acid detection and/or quantification. More particularly, the present invention concerns novel approaches to detection and/or quantification of gene expression, single nucleotide polymorphisms (SNPs), protein-protein interaction, real time PCR and/or pathogen typing.

2. Description of Related Art

Methods of precise and highly sensitive detection and/or quantification of nucleic acids are of use for a variety of medical, forensic, epidemiological, public health, biological warfare and other applications. A variety of molecular biology and genomic techniques would benefit from the availability of precise and sensitive methods for nucleic acid detection and/or quantification.

DNA microarrays provide a platform for exploring the genome, including analysis of gene expression by hybridization with sequence specific oligonucleotide probes attached to chips in precise arrays. (E.g., Schena et al., *Science* 270:467–470, 1995; Shalon et al., *Genome Res.* 6:639–645, 1996; Pease et al., *Proc. Natl. Acad. Sci. USA* 91:5022–26, 1994). Microarray technology is an extension of previous hybridization-based methods, such as Southern and Northern blotting, that have been used to identify and quantify nucleic acids in biological samples (Southern, *J. Mol. Biol.* 98:503–17, 1975; Pease et al., *Proc. Natl. Acad. Sci. USA* 93:10614–19, 1996). Identification of a target nucleic acid in a sample typically involves fluorescent detection of the nucleic acid hybridized to an oligonucleotide at a particular location on the array. Fluorescent detection is too insensitive to detect very low levels of a target nucleic acid in a sample. It is also more qualitative than quantitative. Thus, detection of small changes in the level of expression of a particular gene, as might be attempted for high through-put screening of potential inhibitors and/or activators of gene expression, may not be feasible using a fluorescence detection system with microarrays. More accurate and sensitive methods for nucleic acid quantification are needed.

Real time PCR™ (polymerase chain reaction) is another technique for which accurate and sensitive quantification are needed (e.g., Model 770 TaqMan® system, Applied Biosystems, Foster City, Calif.). Typically, if the target of interest is present, it will be amplified by replication using flanking primers and a nucleic acid polymerase. A probe, which may consist of a complementary oligonucleotide with attached reporter and quencher dyes, is designed to bind to the amplified target nucleic acid between the two primer-binding sites. The nuclease activity of the polymerase cleaves the probe, resulting in an increase in fluorescence of the reporter dye after it is separated from the quencher. PCR based fluorescence detection of target nucleic acids is more sensitive, due to the amplification effect of the technique. However, precise quantification of the amount of target present may be complicated by a variety of factors, such as contaminating nuclease activity or variability in the efficiency of amplification.

Single nucleotide polymorphisms (SNPs) are of increasing interest in molecular biology, genomics and disease diagnostics. SNP detection may be used for haplotype construction in genetic studies to identify and/or detect genes associated with various disease states, as well as drug sensitivity or resistance. SNPs may be detected by a variety of techniques, such as DNA sequencing, fluorescence detection, mass spectrometry or DNA microarray hybridization (e.g., U.S. Pat. Nos. 5,885,775; 6,368,799). Existing methods of SNP detection may suffer from insufficient sensitivity or an unacceptably high level of false positive and/or false negative results. A need exists for more sensitive and accurate methods of detecting SNPs.

Pyrophosphate based detection systems have been used for DNA sequencing (e.g., Nyren and Lundin, *Anal. Biochem.* 151:504–509, 1985; U.S. Pat. Nos. 4,971,903; 6,210,891; 6,258,568; 6,274,320, each incorporated herein by reference). The method uses a coupled reaction wherein pyrophosphate is generated by an enzyme-catalyzed process, such as nucleic acid polymerization. The pyrophosphate is used to produce ATP, in an ATP sulfurylase catalyzed reaction with adenosine 5'-phosphosulphate (APS). The ATP in turn is used for the production of light in a luciferin-luciferase coupled reaction. The present invention provides a novel method of pyrophosphate-based detection for use in SNP detection, gene expression assays, protein-protein interaction, real time PCR, pathogen typing and other applications.

SUMMARY OF THE INVENTION

The present invention fulfills an unresolved need in the art by providing methods for accurately detecting and/or quantifying target analytes, such as nucleic acids, in samples. In preferred embodiments, the number of target nucleic acids in a sample may be accurately determined over a seven order of magnitude range. The disclosed methods provide increased sensitivity and accuracy of target molecule quantification compared to prior art methods. The disclosed methods are generally referred to as "bioluminescence regenerative cycle" or BRC.

In certain embodiments of the invention, the methods may comprise obtaining at least one sample suspected of containing one or more target nucleic acids, generating pyrophosphate by replication of the target nucleic acid, producing light by a bioluminescence regenerative cycle, accumulating the total number of photons produced over different time intervals, comparing the photon accumulation with the background photon emission and determining the number of target nucleic acids in the sample. In particular embodiments, the target nucleic acid is replicated by polymerase chain reaction amplification, although in alternative embodiments any process or reaction that results in the production of pyrophosphate may be coupled to BRC analysis.

In other embodiments of the invention, a target nucleic acid may be covalently or non-covalently attached to another molecule to be quantified, such as a protein, peptide or other ligand. The protein, peptide or ligand may be indirectly quantified, by detecting the attached nucleic acid. Such nucleic acid tagged ligands may be used, for example, to quantify protein-protein binding interactions or any other type of known ligand-receptor binding interaction.

In various embodiments of the invention, the disclosed methods are of use for a wide variety of applications for which nucleic acid quantification is desired. Such applications include, but are not limited to, measuring gene expression levels, detecting and/or quantifying pathogens in a sample, performing real-time PCR™ analysis and detecting single nucleotide polymorphisms (SNPs). In particular embodiments, the BRC method may comprise a rolling circle method of nucleic acid replication.

In particular embodiments of the invention, pyrophosphate is generated by a reaction such as PCR, transcription and/or DNA replication. In preferred embodiments, sequence specific primers are used to limit replication to a particular target nucleic acid in the sample. The sequence specific primers are designed to not bind to other nucleic acids that may be present in the sample. In more preferred embodiments, the pyrophosphate producing reaction is allowed to proceed to completion before BRC analysis. Once the reaction is complete, the pyrophosphate is reacted with APS in the presence of ATP sulfurylase to produce ATP and sulphate. The ATP is reacted with oxygen and luciferin in the presence of luciferase to yield oxyluciferin, AMP and pyrophosphate. For each molecule of pyrophosphate that is cycled through BRC, a photon of light is emitted and one molecule of pyrophosphate is regenerated. Because of the relative kinetic rates of luciferase and ATP sulfurylase, a steady state is reached in which the concentrations of ATP and pyrophosphate and the level of photon output remain relatively constant over an extended period of time. The number of photons may be counted over a time interval to determine the number of target nucleic acids in the sample. The very high sensitivity of BRC is related in part to the integration of light output over time, in contrast to other methods that measure light output at a single time point or at a small number of fixed time points. The ability to vary the length of time over which photon integration occurs also contributes to the very high dynamic range for nucleic acid molecule quantification. The detection noise is also significantly reduced by increasing the length of integration.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

Figure 1:
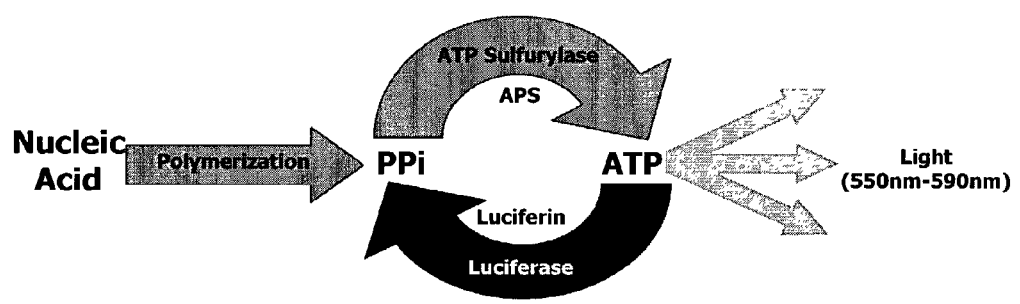
FIG. 1 illustrates an exemplary method for BRC. Nucleic acid polymerization results in the production of pyrophosphate, which is converted to ATP by ATP sulfurylase and APS. The ATP is broken down to pyrophosphate and AMP by luciferin/luciferase with a resulting emission of visible light. The pyrophosphate is recycled to regenerate ATP, resulting in an increase in steady-state luminescence.

Terms that are not otherwise defined herein are used in accordance with their plain and ordinary meaning.

As used herein, "a" or "an" may mean one or more than one of an item.

As used herein, "luminescence" refers to the emission of light that does not derive energy from the temperature of the emitting body (i.e., emission of light other than incandescent light). "Luminescence" includes, but is not limited to, fluorescence, phosphorescence, thermoluminescence, chemiluminescence, electroluminescence and bioluminescence. "Luminescent" refers to an object that exhibits luminescence. In preferred embodiments, the light is in the visible spectrum. However, the present invention is not limited to visible light, but includes electromagnetic radiation of any frequency.

As used herein, the terms "analyte" and "target" mean any compound, molecule or aggregate of interest for detection. Non-limiting examples of targets include a nucleoside, nucleotide, oligonucleotide, polynucleotide, nucleic acid, peptide, polypeptide, protein, carbohydrate, polysaccharide, glycoprotein, lipid, hormone, growth factor, cytokine, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal or any other molecule or atom, without limitation as to size. "Targets" are not limited to single molecules or atoms, but may also comprise complex aggregates, such as a virus, bacterium, *Salmonella*, *Streptococcus*, *Legionella*, *E. coli*, *Giardia*, *Cryptosporidium*, *Rickettsia*, spore, mold, yeast, algae, amoebae, dinoflagellate, unicellular organism, pathogen or cell. In certain embodiments, cells exhibiting a particular characteristic or disease state, such as a cancer cell, may be targets. Virtually any chemical or biological compound, molecule or aggregate could be a target.

"Nucleic acid" means either DNA, RNA, single-stranded, double-stranded or triple stranded and any chemical modifications thereof. Virtually any modification of the nucleic acid is contemplated by this invention. "Nucleic acid" encompasses, but is not limited to, oligonucleotides and polynucleotides. Within the practice of the present invention, a "nucleic acid" may be of any length.

BRC Detection Method

Various embodiments of the invention concern novel methods for quantifying nucleic acid molecules without labeling of any target, capture or probe molecules. Such label free methods are advantageous with respect to sensitivity, expense and ease of use. The BRC methods involve the luminescent detection of pyrophosphate (PPi) molecules released from an enzyme-catalyzed reaction, such as RNA and/or DNA polymerization. As part of the technique, a bioluminescence regenerative cycle (BRC) is triggered by the release of inorganic pyrophosphate (PPi) from polymerization of a nucleic acid.

The regenerative cycle is illustrated in FIG. 1. It involves a first reaction of PPi with APS, catalyzed by ATP-sulfurylase enzyme, which results in the production of ATP and inorganic sulphate. In a second reaction, luciferin and luciferase consume ATP as an energy source to generate light, AMP and oxyluciferin and to regenerate PPi (FIG. 1). Thus, after each BRC cycle, a quantum of light is generated for each molecule of PPi in solution, while the net concentration of ATP in solution remains relatively stable and is proportional to the initial concentration of PPi. In the course of the reactions, APS and luciferin are consumed and AMP and oxyluciferin are generated, while ATP sulfurylase and luciferase remain constant. The invention is not limited as to the type of luciferase used. Although certain disclosed embodiments utilized firefly luciferase, any luciferase known in the art may be used in the disclosed methods.

As a result of the BRC process, the photon emission rate remains steady and is a monotonic function of the amount of PPi in the initial mixture. For very low concentrations of PPi ($10^{-8}$ M or less), the total number of photons generated in a fixed time interval is proportional to the number of PPi molecules. Where PPi is generated by the polymerase catalyzed replication of a target nucleic acid, the number of photons generated in a fixed time interval is proportional to the quantity of the target nucleic acid present in the sample.

The basic concept of enzymatic light generation from PPi molecules was introduced almost two decades ago (Nyren and Lundin, 1985; Nyren, *Anal. Biochem.* 167:235–238, 1987). Pyrophosphate based luminescence has been used for DNA sequencing (Ronaghi et al., *Anal. Biochem.* 242: 84–89, 1996) and SNP detection (Nyren et al., *Anal. Biochem.* 244:367–373, 1997). The present methods provide additional procedures for accurately quantifying specific target nucleic acids in low density arrays or other systems, in the presence of contaminants and detector noise. The novel system and methods have an intrinsic controllable dynamic range up to seven orders of magnitude and are sensitive enough to detect target nucleic acids at attomole ($10^{-18}$) or lower levels.

Theoretical Analysis of BRC

In polymerase-catalyzed reactions, PPi molecules are generated when nucleotides (dNTPs or NTPs) are incorporated into a growing nucleic acid chain. For each addition of a nucleotide, one PPi molecule is cleaved from the dNTP by the polymerase enzyme (e.g. Klenow fragment of DNA polymerase I) and released into the reaction buffer. The reactions catalyzed by DNA and RNA polymerases are shown in Eq. 1 and Eq. 2.

$$(DNA)_n + dNTP \rightarrow (DNA)_{n+1} + PPi \tag{1}$$

$$(RNA)_n + NTP \rightarrow (RNA)_{n+1} + PPi \tag{2}$$

If one assumes that the strand is completely polymerized, then the number of PPi molecules ($N_{PPi}$) released during the process is given by Eq. 3.

$$N_{PPi} = N_{NA} \cdot (L_{NA} - L_P) \tag{3}$$

Where $N_{NA}$ is the total number of primed nucleic acid molecules present in the reaction buffer, and $L_{NA}$ and $L_P$ are respectively the lengths of the nucleic acid chain and the primer.

Enzymatic Bioluminescence Cycle

To generate photons from pyrophosphate, ATP-sulfurylase (Ronesto et al., *Arch. Biochem. Biophys.* 290:66–78, 1994; Beynon et al. *Biochemistry*, 40, 14509–14517, 2001) is used to catalyze the transfer of the adenylyl group from APS to PPi, producing ATP and inorganic sulfate (Eq. 4).

$$PPi + APS \longleftrightarrow ATP + SO_4^{-2} \tag{4}$$

Next, luciferase catalyzes the slow consumption of ATP, luciferin and oxygen to generate a single photon ($\lambda_{max}$=562 nm, Q.E.≈0.88) per ATP molecule, regenerating a molecule of PPi and producing AMP, $CO_2$ and oxyluciferin (Eq. 5). (Brovko et al., *Biochem.* (Moscow) 59:195–201, 1994)

$$ATP + Luciferin + O_2 \rightarrow AMP + oxyluciferin + CO_2 + h\nu + PPi \tag{5}$$

Because the luciferase reaction is significantly slower than the ATP-sulfurylase reaction (FIG. 3A), in the presence of sufficient amounts of the substrates APS and luciferin a steady state cycle should be maintained, in which the concentration of ATP and the resulting levels of light emission remain relatively constant for a considerable time.

Figure 2:
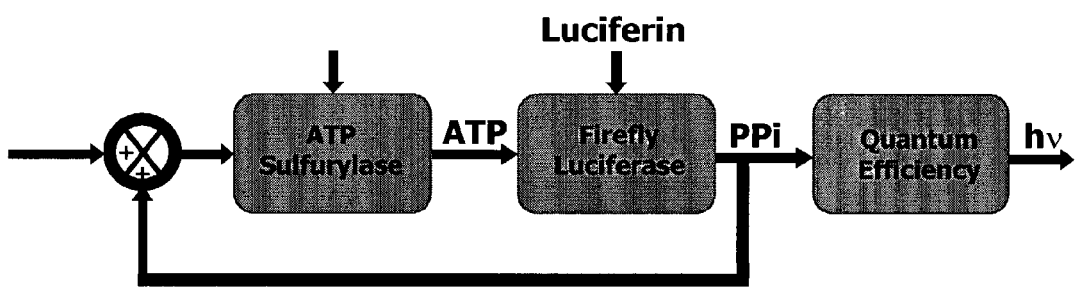
FIG. 2 shows a bioluminescence regenerative cycle block diagram of the ATP sulfurylase and luciferase catalyzed reactions in BRC.

This steady state cycle is indicated schematically in FIG. 2. Because the steady-state photon emission is proportional to the initial concentration of PPi, the presence of minute amounts of PPi produced by a polymerase or other reaction should result in a detectable shift in baseline luminescence, even in the presence of considerable amounts of noise. The number of photons generated over time by the BRC cycle can potentially be orders of magnitude higher than the initial number of PPi molecules, which makes the system extremely sensitive compared to prior art methods of nucleic acid quantification. The increased sensitivity is provided by having a time-dependent amplification of light emission for each molecule of PPi present at the start of the BRC cycle.

Photon Generation Rate

Figure 3A:
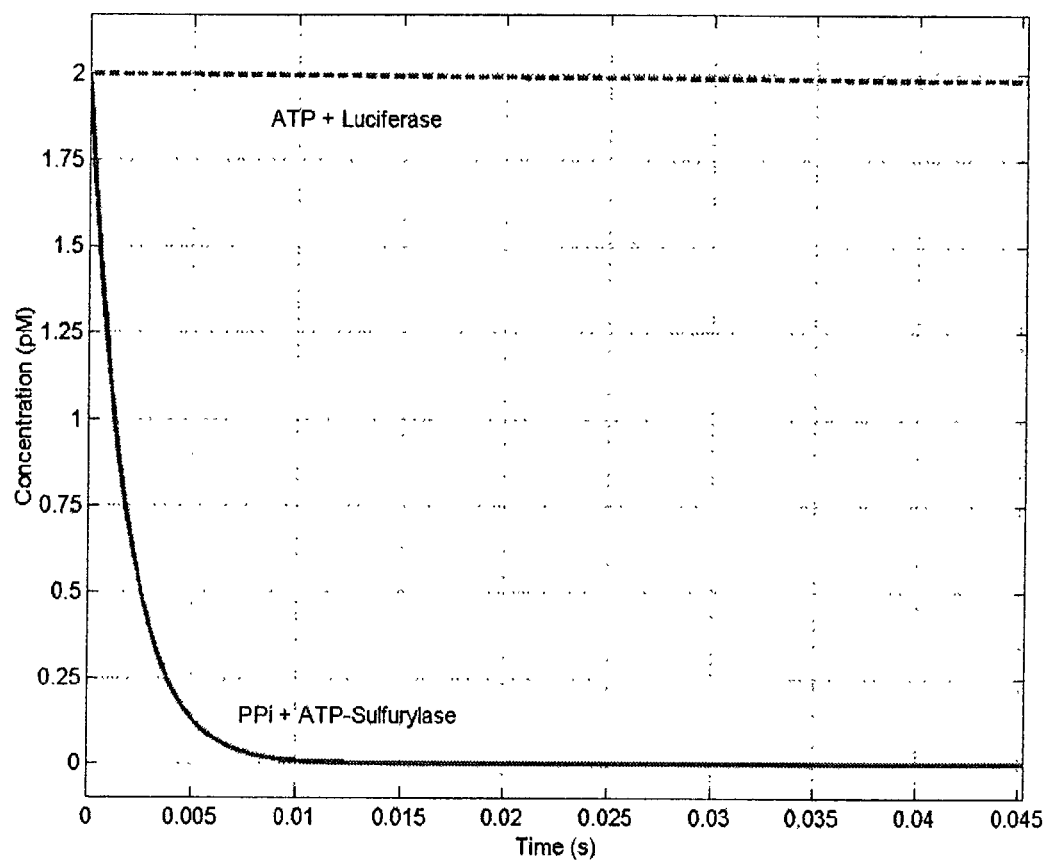
FIG. 3A shows a simulation of a comparison between the rates of ATP-sulfurylase PPi consumption and luciferase ATP consumption (luciferin=0.1 mM, APS=0.1 mM), based on the kinetic properties of the enzymes.

The photon generation rate of the system may be determined from the kinetics and steady state characteristics of the enzymes ATP sulfurylase and luciferase (Ronesto et al., 1994; Beynon et al., 2001; Brovko et al., 1994). As shown in FIG. 3A, in the presence of saturating concentrations of APS and luciferin, the ATP-sulfurylase reaction is orders of magnitude faster than the luciferase reaction. Thus, the rate of photon generation will be limited by the kinetics of luciferase rather than ATP-sulfurylase (FIG. 3A). A simplified equation expressing light intensity (I) for the BRC process is shown in Eq. 6.

$$I = \frac{1}{\alpha} \cdot \frac{d}{dt}\left(\frac{N_{ATP}}{V}\right) = \left(\frac{k_L}{\alpha V}\right) N_{ATP} \tag{6}$$

$N_{ATP}$ is the number of ATP molecules in the solution, $k_L$ is the turnover rate constant of luciferase, V is the volume of the solution, and $\alpha$ is the quantum efficiency of the bioluminescence process.

Figure 3B:
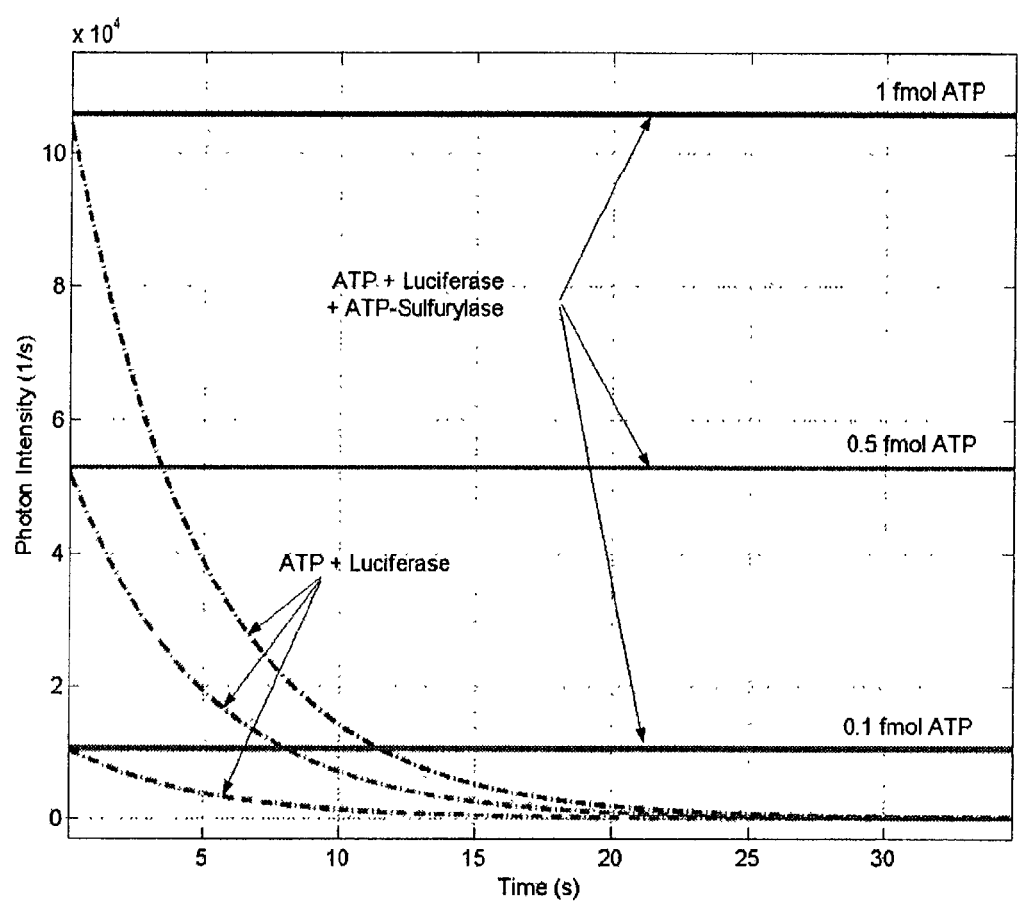
FIG. 3B shows a simulation of a comparison between luciferase generated light intensity in the presence and absence of ATP sulfurylase and APS at different starting concentrations of ATP (luciferin=0. 1 mM, APS=0.1 mM), based on the kinetic properties of the enzymes.

If ATP-sulfurylase was not present in the buffer, the light intensity would never reach a steady state and would simply decay as a function of time. In the presence of ATP-sulfurylase and APS, any decrease in the concentration of ATP will be compensated almost instantly by reaction of the generated PPi molecule with APS to regenerate ATP. This will cause the system to stay in a quasi-equilibrium state, where the concentrations of ATP and PPi remain relatively constant. At the same time, the luciferase reaction is constantly occurring and photons are emitted in a steady state fashion (FIG. 3B). If the concentrations of APS and luciferin are high enough to assure saturation, then the steady state light intensity is given by Eq. 7.

$$I = \left(\frac{k_L}{\alpha V}\right)(N_{PPi})_0 \tag{7}$$

$(N_{PPi})_0$ is the initial number of PPi molecules generated from the polymerization or other process. Combining equations 3 and 7 gives Eq. 8.

$$I = \left(\frac{k_L}{\alpha V}\right) N_{NA} \cdot (L_{NA} - L_P). \tag{8}$$

Equation 8 shows the proportionality between the generated light intensity and the initial number of nucleic acid molecules. If the number of photons detected is accumulated for a time interval T (integration time), the total number of photons generated ($N_{ph}$) is given by Eq. 9.

$$N_{ph} = \left(\frac{k_L}{\alpha V}\right) T \cdot N_{NA} \cdot (L_{NA} - L_P). \tag{9}$$

According to Eq. 9, the number of photons received by the detector (e.g. CCD camera) depends on the integration time and the number of target molecules present in the solution. By controlling the integration time the sensitivity of the system can be increased to any desired level limited by the saturation of the optical system. The dynamic range of the sensor system may therefore be proportionately enhanced.

Noise and Background Contamination

There are two phenomena possible in BRC that might potentially interfere with the performance and sensitivity of nucleic acid detection. One is the possibility of PPi and/or ATP contamination from the chemicals included in the buffer solution. The other is the noise of the detector (e.g. thermal noise and/or shot noise in a photodiode system). The effects of ATP and PPi contamination on light emission may be modeled by modifying Eq. 8 to account for an initial existing number of PPi molecules $C_{PPi}$, resulting in Eq. 10.

$$I = \left(\frac{k_L}{\alpha V}\right) \cdot [N_{NA} \cdot (L_{NA} - L_P) + C_{PPi}]. \tag{10}$$

Although $C_{PPi}$ is relatively low for common bioluminescence measurements (on the order of 0.1 to 10 femtomoles), it can be an order of magnitude higher than the target nucleic acid concentration. It is also possible to have variation between experiments in the value of $C_{PPi}$ of as much as 300%. To eliminate the effects of any possible contamination, the light intensity of the system is initially measured in the absence of any PPi generated from polymerization. This serves as an initial reference point for measuring the catalytically produced PPi. If the light intensity in the reference state is $I_r$, by combining equations 9 and 10 the value of $N_{NA}$ may be calculated from Eq. 11.

$$N_{NA} = \left(\frac{\alpha V}{k_L}\right) \frac{I - I_r}{L_{NA} - L_P} \tag{11}$$

In terms of number of photons detected;

$$N_{NA} = \left(\frac{\alpha V}{k_L}\right) \frac{N_{ph} - N_{phr}}{T \cdot (L_{NA} - L_p)} \tag{12}$$

To account for the noise of the system, it is assumed that the total noise of the detector n(t) is random and has a normal distribution $N(0,\sigma)$, with a mean of zero and a standard deviation of $\sigma$. Thus, the apparent light intensity in the presence of detector noise is given by Eq. 13.

$$I(t) = \left(\frac{k_L}{\alpha V}\right) N_{NA} \cdot (L_{NA} - L_P) + n(t), \tag{13}$$

Integrating Eq. 13 over a time interval T, $$N'_{NA} = \left(\frac{\alpha V}{k_L}\right) \frac{\int I(\tau) d\tau}{(L_{NA} - L_P) \cdot T} \tag{14}$$

$$= \left(\frac{\alpha V}{k_L}\right) \frac{N_{ph} - N_{phr} + \int_T (n_1(\tau) - n_2(\tau)) d\tau}{(L_{NA} - L_p) \cdot T}$$

where $n_1(t)$ and $n_2(t)$ are the noise introduced by the detector in the actual experiment and reference respectively. $n_1(t)$ and $n_2(t)$ are uncorrelated but have the same normal distribution of $N(0,\sigma)$. $N'_{NA}$ is the measured nucleic acid quantity. Equation 14 can be rewritten as $$N'_{NA} = N_{NA} + n'(t), \tag{15}$$

where n'(t) is a normal distribution defined as $$N'_{NA} - N_{NA} = n'(t) \rightarrow N\left(0, \sqrt{\frac{2}{T}} \cdot \frac{\alpha V \sigma}{k_L (L_{NA} - L_P)}\right) \tag{16}$$

As shown in Eq. 16, the difference between the estimated and actual quantity of the target nucleic acid (measurement error) has a normal distribution. The standard deviation of error is a function of chemistry ($k_L$ of luciferase in the assay), noise of the detector, and integration time. To achieve a selected level of error tolerance, the required integration time for a given chemistry and specific level of detector noise may be calculated.

The above analysis provides a quantitative basis for determination of the number of target nucleic acid (or other) molecules present in a sample, accounting for the presence of contaminants and noise in the system. The resulting method provides a highly sensitive and accurate procedure for determining the number of target molecules in a given sample. These methods are broadly applicable for a variety of techniques in which quantitative detection of target molecules is desired.

Nucleic Acids

Samples comprising nucleic acids may be prepared by any technique known in the art. In certain embodiments, the analysis may be performed on crude sample extracts, containing complex mixtures of nucleic acids, proteins, lipids, polysaccharides and other compounds. Such samples are likely to contain contaminants that could potentially interfere with the BRC process. In preferred embodiments, nucleic acids may be partially or fully separated from other sample constituents before initiating the BRC analysis.

Methods for partially or fully purifying DNA and/or RNA from complex mixtures, such as cell homogenates or extracts, are well known in the art. (See, e.g., Guide to Molecular Cloning Techniques, eds. Berger and Kimmel, Academic Press, New York, N.Y., 1987; Molecular Cloning: A Laboratory Manual, 2nd Ed., eds. Sambrook, Fritsch and Maniatis, Cold Spring Harbor Press, Cold Spring Harbor, N.Y., 1989). Generally, cells, tissues or other source material containing nucleic acids are first homogenized, for example by freezing in liquid nitrogen followed by grinding in a mortar and pestle. Certain tissues may be homogenized using a Waring blender, Virtis homogenizer, Dounce homogenizer or other homogenizer. Crude homogenates may be extracted with detergents, such as sodium dodecyl sulphate (SDS), Triton X-100, CHAPS (3-[(3-cholamidopropyl)-dimethylammonio]-1-propane sulfonate), octylglucoside or other detergents known in the art. As is well known, nuclease inhibitors such as RNase or DNase inhibitors may be added to prevent degradation of target nucleic acids.

Extraction may also be performed with chaotrophic agents such as guanidinium isothiocyanate, or organic solvents such as phenol. In some embodiments, protease treatment, for example with proteinase K, may be used to degrade cell proteins. Particulate contaminants may be removed by centrifugation or ultracentrifugation. Dialysis against aqueous buffer of low ionic strength may be of use to remove salts or other soluble contaminants. Nucleic acids may be precipitated by addition of ethanol at –20° C., or by addition of sodium acetate (pH 6.5, about 0.3 M) and 0.8 volumes of 2-propanol. Precipitated nucleic acids may be collected by centrifugation or, for chromosomal DNA, by spooling the precipitated DNA on a glass pipet or other probe. The skilled artisan will realize that the procedures listed above are exemplary only and that many variations may be used, depending on the particular type of nucleic acid to be analyzed.

In certain embodiments, the nucleic acids to be analyzed may be naturally occurring DNA or RNA molecules. Virtually any naturally occurring nucleic acid may be analyzed by the disclosed methods including, without limit, chromosomal, mitochondrial or chloroplast DNA or ribosomal, transfer, heterogeneous nuclear or messenger RNA. Nucleic acids may be obtained from either prokaryotic or eukaryotic sources by standard methods known in the art. Alternatively, nucleic acids of interest may be prepared artificially, for example by PCR™ or other known amplification processes or by preparation of libraries such as BAC, YAC, cosmid, plasmid or phage libraries containing nucleic acid inserts. (See, e.g., Berger and Kimmel, 1987; Sambrook et al., 1989.) The source of the nucleic acid is unimportant for purposes of performing BRC analysis and it is contemplated within the scope of the invention that nucleic acids from virtually any source may be analyzed using the BRC process.

Methods of Immobilization

In various embodiments, the nucleic acids to be analyzed may be attached to a solid surface (or immobilized). Immobilization of nucleic acids may be achieved by a variety of methods involving either non-covalent or covalent attachment between the nucleic acid and the surface. In an exemplary embodiment, immobilization may be achieved by coating a surface with streptavidin or avidin and the subsequent attachment of a biotinylated polynucleotide (Holmstrom et al., Anal. Biochem. 209:278–283, 1993). Immobilization may also occur by coating a silicon, glass or other surface with poly-L-Lys (lysine), followed by covalent attachment of either amino- or sulfhydryl-modified nucleic acids using bifunctional crosslinking reagents (Running et al., BioTechniques 8:276–277, 1990; Newton et al., Nucleic Acids Res. 21:1155–62, 1993). Amine residues may be introduced onto a surface through the use of aminosilane for cross-linking.

Immobilization may take place by direct covalent attachment of 5'-phosphorylated nucleic acids to chemically modified surfaces (Rasmussen et al., Anal. Biochem. 198:138–142, 1991). The covalent bond between the nucleic acid and the surface is formed by condensation with a water-soluble carbodiimide. This method facilitates a predominantly 5'-attachment of the nucleic acids via their 5'-phosphates.

DNA is commonly bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule. DNA may be bound directly to membrane surfaces using ultraviolet radiation. Other non-limiting examples of immobilization techniques for nucleic acids are disclosed in U.S. Pat. Nos. 5,610,287, 5,776,674 and 6,225,068.

The type of surface to be used for immobilization of the nucleic acid is not limiting. In various embodiments, the immobilization surface may be magnetic beads, non-magnetic beads, a planar surface, or any other conformation of solid surface comprising almost any material, so long as the material is sufficiently durable and inert to allow the BRC process to occur. Non-limiting examples of surfaces that may be used include glass, silica, silicate, PDMS, silver or other metal coated surfaces, nitrocellulose, nylon, activated quartz, activated glass, polyvinylidene difluoride (PVDF), polystyrene, polyacrylamide, other polymers such as poly (vinyl chloride), poly(methyl methacrylate) or poly(dimethyl siloxane), and photopolymers which contain photoreactive species such as nitrenes, carbenes and ketyl radicals capable of forming covalent links with nucleic acids (See U.S. Pat. Nos. 5,405,766 and 5,986,076).

Bifunctional cross-linking reagents may be of use in various embodiments, such as attaching a nucleic acid to a surface. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Polymerases

In certain embodiments, the disclosed methods may involve binding of a DNA polymerase to a primer molecule and the catalyzed addition of nucleotide precursors to the 3' end of a primer. Non-limiting examples of polymerases of potential use include DNA polymerases, RNA polymerases, reverse transcriptases, and RNA-dependent RNA polymerases. The differences between these polymerases in terms of their requirement or lack of requirement for primers and promoter sequences are known in the art.

Non-limiting examples of polymerases that may be of use include *Thermatoga maritima* DNA polymerase, AmplitaqFS™ DNA polymerase, Taquenase™ DNA polymerase, ThermoSequenase™, Taq DNA polymerase, Qbeta™ replicase, T4 DNA polymerase, *Thermus thernophilus* DNA polymerase, RNA-dependent RNA polymerase and SP6 RNA polymerase. Commercially available polymerases including Pwo DNA Polymerase from Boehringer Mannheim Biochemicals (Indianapolis, Ind.); Bst Polymerase from Bio-Rad Laboratories (Hercules, Calif.); IsoTherm™ DNA Polymerase from Epicentre Technologies (Madison, Wis.); Moloney Murine Leukemia Virus Reverse Transcriptase, Pfu DNA Polymerase, Avian Myeloblastosis Virus Reverse Transcriptase, *Thermus flavus* (Tfl) DNA Polymerase and *Thermococcus litoralis* (Tli) DNA Polymerase from Promega (Madison, Wis.); RAV2 Reverse Transcriptase, HIV-1 Reverse Transcriptase, T7 RNA Polymerase, T3 RNA Polymerase, SP6 RNA Polymerase, RNA Polymerase *E. coli*, *Thermus aquaticus* DNA Polymerase, T7 DNA Polymerase +/−3'→5' exonuclease, Klenow Fragment of DNA Polymerase I, Thermus 'ubiquitous' DNA Polymerase, and DNA polymerase I from Amersham Pharmacia Biotech (Piscataway, N.J.).

As is known in the art, various polymerases have an endogenous 3'–5' exonuclease activity that may be used for proof-reading newly incorporated nucleotides. Because a molecule of pyrophosphate is generated for each nucleotide incorporated into a growing chain, regardless of whether or not it is subsequently removed, in certain embodiments of the invention it may be preferred to use polymerases that are lacking exonuclease or proof-reading activity.

Methods of using polymerases and compositions suitable for use in such methods are well known in the art (e.g., Berger and Kimmel, 1987; Sambrook et al., 1989).

Primers

Where primers are required to initiate polymerase activity, they may be obtained by any method known in the art. Generally, primers are between ten and twenty bases in length, although longer primers may be employed. In certain embodiments, primers are designed to be exactly complementary in sequence to a known portion of a target nucleic acid, preferably at or close to the 3' end of the target nucleic acid. Methods for synthesis of primers of any sequence are known, for example using an automated nucleic acid synthesizer employing phosphoramidite chemistry. Such instruments may be obtained from commercial sources, such as Applied Biosystems (Foster City, Calif.) or Millipore Corp. (Bedford, Mass.).

Detectors

In various embodiments of the invention, photons generated by BRC may be quantified using a detector, such as a charge coupled device (CCD). Other exemplary detectors include photodiodes, avalanche photodiodes, photomultiplier tubes, multianode photomultiplier tubes, phototransistors, vacuum photodiodes, silicon photodiodes, and CCD cameras.

In certain embodiments of the invention, a highly sensitive cooled CCD detector may be used. The cooled CCD detector has a probability of single-photon detection of up to 80%, a high spatial resolution pixel size (5 microns), and sensitivity in the visible through near infrared spectra. (Sheppard, Confocal Microscopy: Basic Principles and System Performance in: Multidimensional Microscopy, P. C. Cheng et al. eds., Springer-Verlag, New York, N.Y. pp. 1–51, 1994.) In another embodiment of the invention, a coiled image-intensified coupling device (ICCD) may be used as a photodetector that approaches single-photon counting levels (U.S. Pat. No. 6,147,198). A small number of photons triggers an avalanche of electrons that impinge on a phosphor screen, producing an illuminated image. This phosphor image is sensed by a CCD chip region attached to an amplifier through a fiber optic coupler.

In some embodiments of the invention, an avalanche photodiode (APD) may be made to detect low light levels. The APD process uses photodiode arrays for electron multiplication effects (U.S. Pat. No. 6,197,503). The invention is not limited to the disclosed embodiments and it is contemplated that any light detector known in the art that is capable of accumulating photons over a time interval may be used in the disclosed methods and apparatus.

In all of the above embodiments the generated photons from the sample can either reach the detector directly or be guided and/or focused onto the detector by a secondary system such as a number of lenses, reflecting mirror systems, optical waveguides and optical fibers or a combination of those.

EXAMPLES

Example 1

BRC Assay

Sample Preparation

Total RNA extracts may be obtained from blood, tissues or cell lines using commercially available kits (e.g., Ambion, Austin, Tex.; Qiagen, Valencia, Calif.; Promega, Madison, Wis.). CDNA may be synthesized using a SuperScript™ or other commercial kit (Invitrogen Life Technologies, Austin, Tex.). Where preferred, polyadenylated mRNA may be purified by oligo(dT) column chromatography or other known methods.

In an exemplary embodiment, first strand cDNA synthesis employed an RNA/primer mixture containing 5 μl total RNA and 1 μl of 0.5 μg/μl oligo(dT) random primer or gene specific primer, incubated at 70° C. for 10 min and then placed on ice for at least 1 min. A reaction mixture containing 2 μl 10× buffer (0.1 M Tris-Acetate pH 7.75, 5 mM EDTA, 50 mM Mg-acetate, 2 mM kinase free dNTP and 0.1 M dithiothreitol) in which dATP was replaced with (α-thio dATP was added to the RNA/primer mixture, mixed gently, collected by brief centrifugation and then incubated at 42° C. for 5 min. After addition of 200 U of SuperScript II reverse transcriptase, the tube was incubated at 40° C. for 15 min. The reaction was terminated by heating at 70° C. for 15 min and then chilling on ice. The dNTP used in cDNA synthesis should be kinase free. In preferred embodiments dATP is replaced with alpha-thio dATP or analogs that are not good substrates for luciferase.

An aliquot of synthesized cDNA was added to 50 μl of reaction mixture (see Ronaghi et al., *Anal. Biochem.* 242: 84–89, 1996 with modifications) containing 250 ng luciferase (Promega, Madison, Wis.), 50 mU ATP sulfurylase (Sigma Chemical Co., St. Louis, Mo.), 2 mM dithiothreitol, 100 mM Tris-Acetate pH 7.75, 0.5 mM EDTA, 0.5 mg BSA, 0.2 mg polyvinylpyrrolidone ($M_r$ 360.000), 10 μg D-luciferin (Biothema, Dalaro, Sweden), 5 mM magnesium acetate and 10 attomole to 0.01 attomole purified pyrophosphate or ATP. The addition of very low amounts of pyrophosphate or ATP (or analogs) was found to be important to decrease background light emission from the reaction mixture. Although the precise mechanism is unknown, BRC performed without adding small amounts of ATP or PPi consistently exhibited background luminescence that precluded accurate measurement of target nucleic acids present in amounts of about a femtomole or lower. Inorganic pyrophosphate present in the cDNA sample as a result of polymerase mediated dNTP incorporation was converted to ATP by sulfurylase. The ATP was used to generate light in a luciferin/luciferase reaction.

The generated light intensity over a time interval may be used to calculate the number of target molecules converted to cDNA by reverse transcriptase. In this exemplary process, the total amount of polyadenylated RNA present in the sample was determined, using oligo(dT) random primers. The presence of specific target nucleic acids may be determined using sequence specific primers, as detailed below.

Synthesis and Purification of Sequence Specific Oligonucleotide Primers

The following oligonucleotides were synthesized and HPLC purified by MWG Biotech (High Points, N.C.).

```
B-MBPup
Biotin-5'-CGGCGATAAAGGCTATAACGG-3'      (SEQ ID NO:1)

MBPup
5'-CGGCGATAAAGGCTATAACGG-3'             (SEQ ID NO:2)

B-MBPR1
Biotin-5'-CTGGAACGCTTTGTCCGGGG-3'       (SEQ ID NO:3)

MBPR1
5'-CTGGAACGCTTTGTCCGGGG-3'              (SEQ ID NO:4)

oligo-loop
5'TTTTTTTTTTTTTTTTTTTTGCTGGAATTCGTCAG   (SEQ ID NO:5)
ACTGGCCGTCGTTTTACAACGGAACGGCAGCAAAATG
TTGC-3'
```

Template Preparation

Biotinylated PCR products were prepared from bacterial extracts containing pMAL vector (New England Biolabs, Beverly, Mass.) (Pourmand et al. 1998, Autoimmunity 28; 225–233) by standard techniques, using MBPup and biotinylated B-MBPR1 or MBPR1 and biotinylated B-MBPup as PCR primers. The PCR products were immobilized onto streptavidin-coated superparamagnetic beads (Dynabeads™ M280-Streptavidin, Dynal A. S., Oslo, Norway). Single-stranded DNA was obtained by incubating the immobilized PCR product in 0.10 M NaOH for 3 min to separate strands and then removing the supernatant.

Strand Extension

The immobilized single stranded PCR product was resuspended in annealing buffer (10 mM Tris-acetate pH 7.75, 2 mM Mg-acetate) and placed into wells of a microtiter plate. Five pmol of the BRC primers MBP-up (SEQ ID NO:2) or MBPR1 (SEQ ID NO:4) were added to the immobilized strand obtained from the PCR reaction (depending on what set of biotinylated PCR primers was used). Hybridization of the template and primers was performed by incubation at 95° C. for 3 min, 72° C. for 5 min and then cooling to room temperature. Extension occurred in the presence of 10 U exonuclease-deficient (exo-) Klenow DNA polymerase (New England Biolabs, Beverly, Mass.) and addition of all four deoxynucleoside triphosphates to the extension mixture (0.14 mM final concentration). As discussed above, α-thio dATP was substituted for dATP to prevent interference with the luciferase reaction. After extension, the contents of each well were serially diluted for comparison of light emission as a function of PPi concentration.

Figure 5:
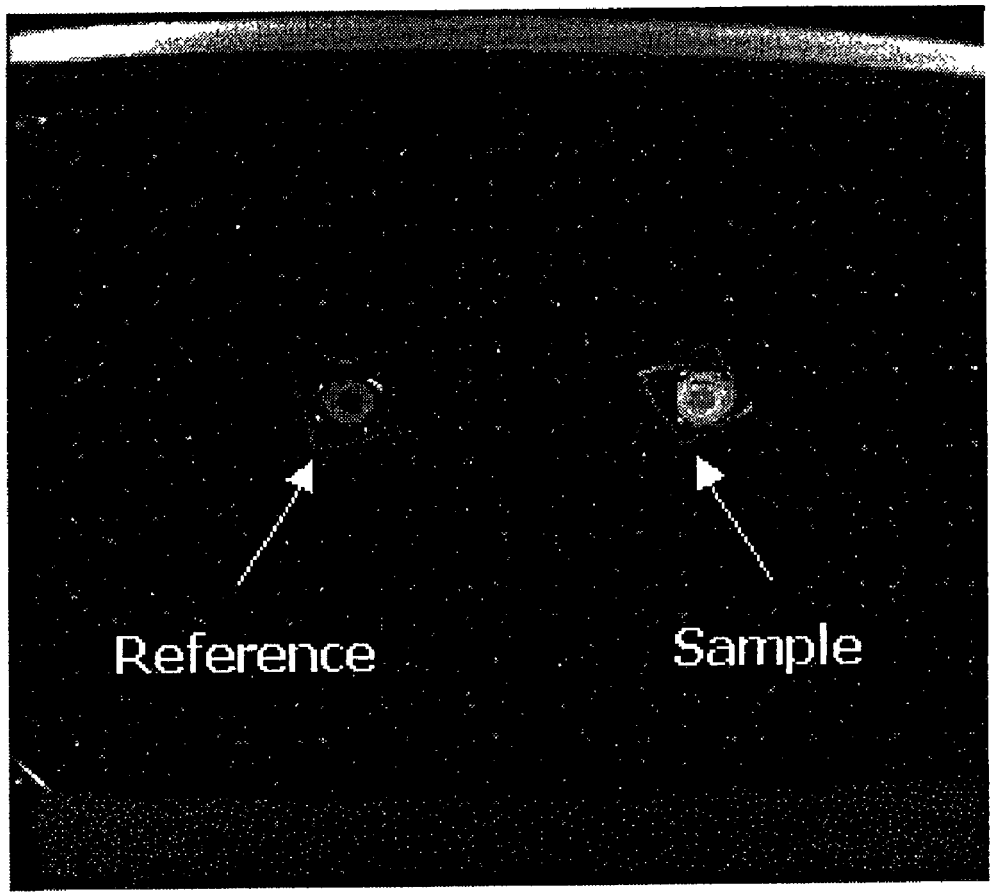
FIG. 5 shows an exemplary result of a BRC assay, comparing light emission from a 0.1 pmol sample with a reference standard.
Figure 6:
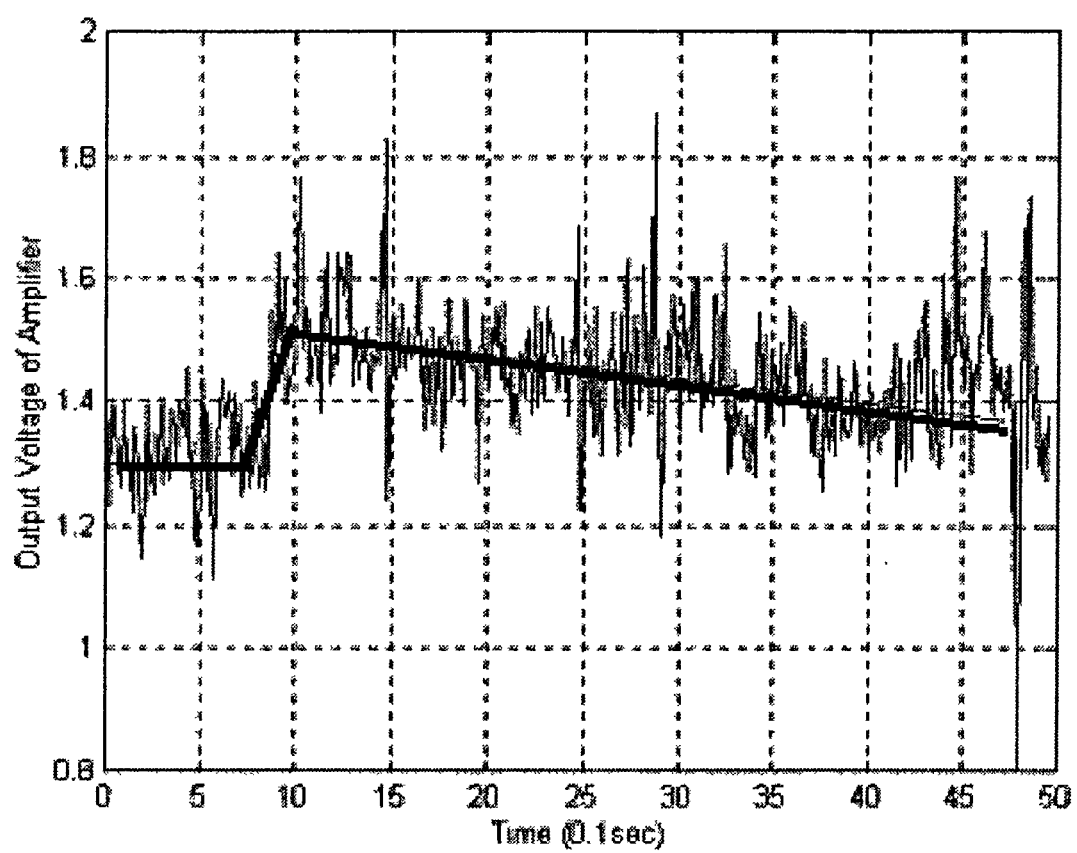
FIG. 6 shows the increase in steady state light emission from a 10 fmol (femtomole) sample. Random noise in the light emission can be filtered out by detecting a steady-state change in the baseline level of light emission.

In an exemplary embodiment, extension and real-time luminometric monitoring were performed at 25° C. in a Xenogen instrument (Xenogen, Menlo Park, Calif.). A luminometric reaction mixture was added to the substrate with different concentrations of extended primed single-stranded DNA or self primed oligonucleotide. The luminometric assay mixture (40 μl) contained 0.4 μg luciferase (Promega, Madison, Wis.), 15 mU recombinant ATP sulfurylase (Sigma Chemicals, St. Louis, Mo.), 0.1 M Tris-acetate (pH 7.75), 0.5 mM EDTA, 5 mM Mg-acetate, 0.1% (w/v) bovine serum albumin, 1 mM dithiothreitol, 10 μM adenosine 5'-phosphosulfate (APS) (Biolog, Alexis Biochemicals, Carlsbad, Calif.), 0.4 mg polyvinylpyrrolidone/ml (molecular weight 360000) and 100 μg D-luciferin/ml (BioThema AB, Haninge, Sweden). Emitted light was detected in real-time and measured after 1 second (FIG. 5). FIG. 5 and FIG. 6 show a Xenogen image and amplified signal output for a 0.1 picomole sample of target nucleic acid. Similar images have been obtained with target nucleic acid samples as low as 0.1 attomole. Note that using the modified protocol with 0.01 attomole to 10 attomole purified pyrophosphate or ATP added, the background light intensity is essentially zero. FIG. 6 shows that even in the presence of random noise background that is of approximately the same order of magnitude as the actual signal, the pyrophosphate induced signal can still be detected as a shift in the baseline level of the light output.

Detection Devices

The number of the photons generated by BRC may be measured using any known type of photodetector. Common devices that may be used include photodiodes, photomultiplier tubes (PMTs), charge coupled devices (CCDs), and photo-resistive materials. Luciferase-catalyzed photon generation has a quantum yield (Q.E.) of approximately 0.88, with the wavelength maximum depending on the type of luciferase used. For various types of luciferase, that can be anyplace within the visible range of the spectrum. Exemplary embodiments used firefly luciferase, which has a maximum intensity at 562 nm.

Figure 4:
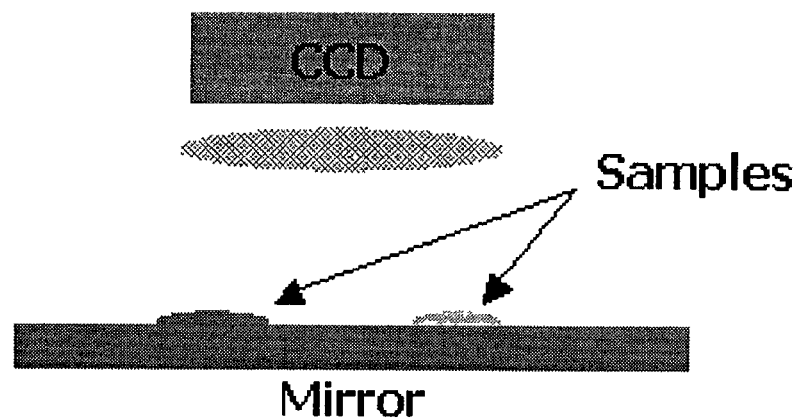
FIG. 4 illustrates an exemplary apparatus and system for performing the BRC method.
Figure 4:
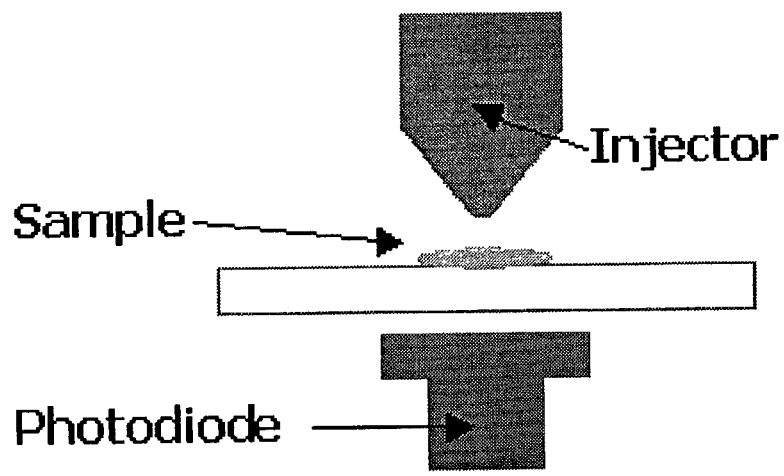

The photosensitive device is typically either in direct proximity of the BRC reaction to directly receive incident photons, or relatively far from the buffer with a light coupling device (e.g. optical fiber or mirror system) capable of directing light from the sample to the detector (FIG. 4). In an exemplary embodiment, a UDT-PIN-UV-50-9850-1 photodiode (Hamamatsu Corp., Hamamatsu, Japan) was used with a transimpedance amplifier with a gain of $10_8$ volts/amp.

Example 2

SNP detection Using Total RNA Templates

Figure 7:
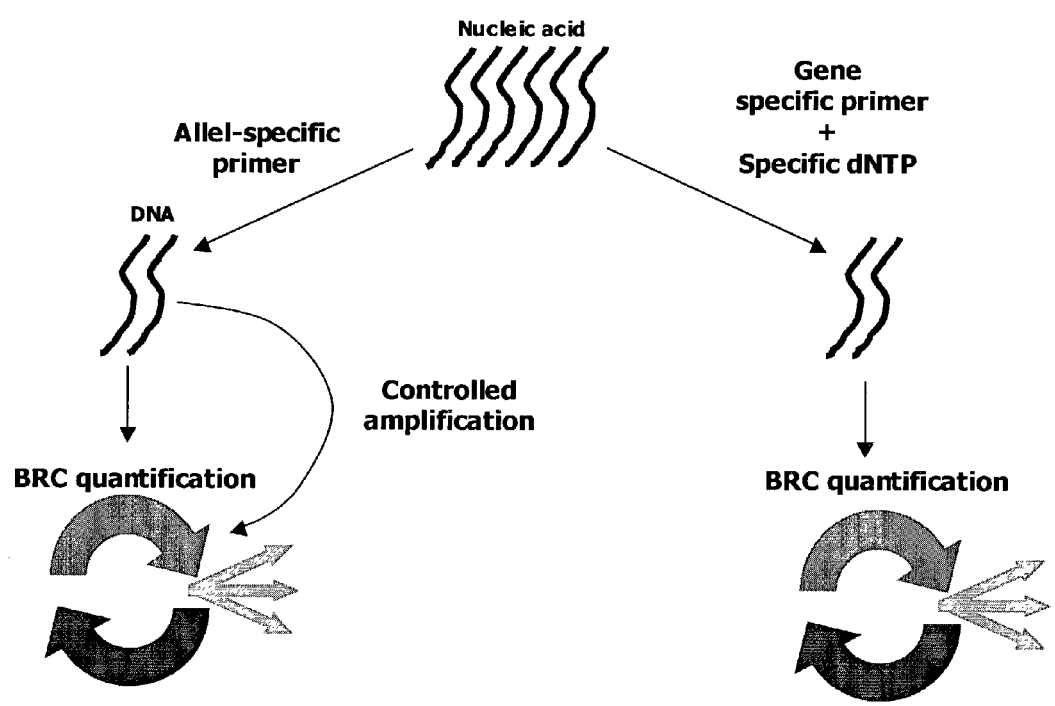
FIG. 7 shows an exemplary embodiment of BRC applied to SNP detection.

SNPs have been detected by hybridization of total RNA incubated with gene specific or allele specific primers and/or probes (Higgins et al, *Biotechniques* 23:710–714, 1997; Newton et al. *Lancet* 2:1481–1483, 1989; Goergen et al, *J Med Virol* 43:97–102, 1994; Newton et al, *Nucleic Acids Res* 17:2503–2516, 1989). Using the methods disclosed herein, SNPs may be detected by BRC, using sequence specific extension primers designed to bind to the template with the 3' end of the primer located over the base of interest (SNP site) (FIG. 7). In preferred embodiments, the primer sequence is selected so that the end of the primer to which nucleotides will be attached is base-paired with the polymorphic site. In certain embodiments, where the SNP is located in a coding sequence, the primer may be allowed to hybridize to total RNA or polyadenylated mRNA. (Alternatively, to detect non-coding SNPs genomic DNA or PCR amplified genomic DNA may be used as the target.) The template/primer fragments are used as the substrate for a primer extension reaction (e.g., Sokolov, *Nucleic Acids Res* 18:3671, 1989) in the presence of reverse transcriptase. If a target sequence is present that is complementary to the sequence specific primer, extension occurs and pyrophosphate is generated. An aliquot of the reaction product is added to a BRC reaction mixture as disclosed above. Extension products (PPi) are detected as disclosed above, allowing identification of the SNP in the target nucleic acid.

Typically SNPs exist in one of two alternative alleles. The allelic variant of the SNP may be identified by performing separate BRC reactions with primers specific for each of the SNP variants. In an alternative embodiment, the SNP allele may be identified using a gene specific primer that binds immediately upstream of the SNP site, allowing extension to occur in the presence of a single type of dXTP (or α-thio dATP) (FIG. 7). Extension will occur if the added dXTP is complementary to the SNP nucleotide.

Example 3

SNP Detection Using cDNA Templates

In alternative embodiments, SNPs may be detected from cDNA templates. Complementary DNAs may be prepared by standard methods, as disclosed above, and hybridized with gene specific or allele specific primers (FIG. 7) in 20 mM Tris-HCl (pH 7.5), 8 mM $MgCl_2$ or other standard conditions. The primers are designed to bind to the template with the 3' end located over the polymorphic position. The template/primer fragments are then used as substrates in a primer extension reaction, as discussed above. Pyrophosphate generation, detected by the BRC reaction, indicates the presence of a SNP sequence that is complementary to the primer. As discussed above, gene specific primers also may be used in combination with single dXTPs.

Example 4

Pathogen Typing by BRC

Figure 8:
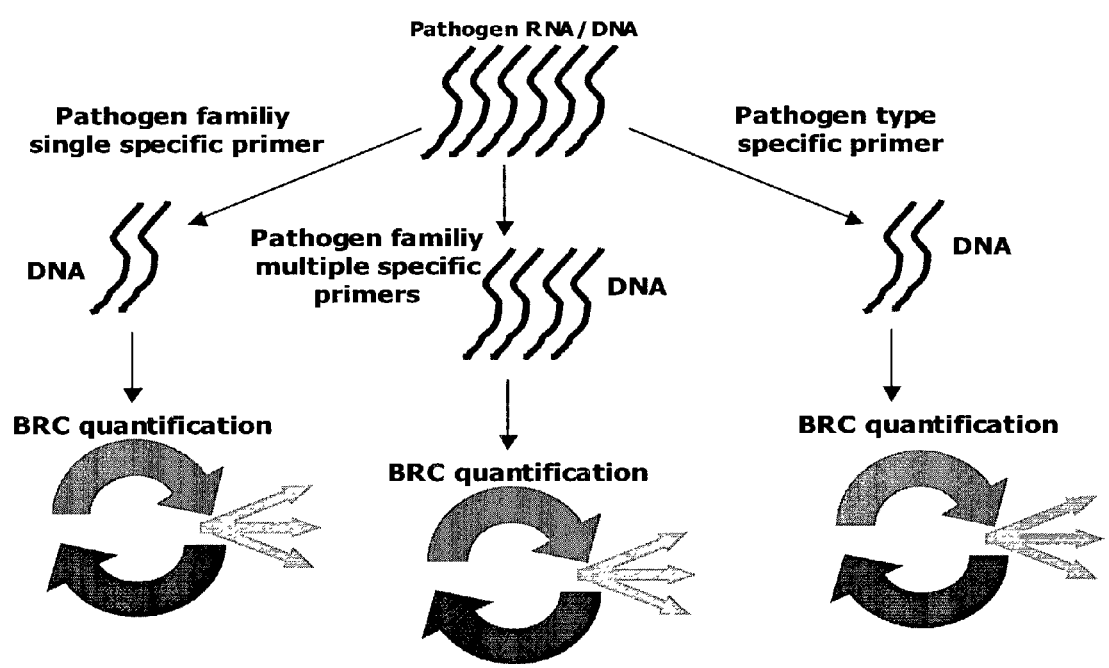
FIG. 8 shows an exemplary embodiment of BRC applied to pathogen detection.

FIG. 8 illustrates embodiments of the invention in which BRC can be used to identify, type and/or quantify target pathogens in a sample. Total RNA or genomic DNA of the pathogenic organism may be incubated with pathogen specific primers (FIG. 8). In some embodiments, a single primer may be specific for one type of pathogen, or may be specific for a family of pathogens. Alternatively, multiple primers specific for different sub-types of a family of pathogens may be used. After hybridization in a suitable buffer, primer extension occurs with either reverse transcriptase or DNA polymerase, as disclosed above. The presence of a target pathogen type, or a member of a family of pathogens, is detected by luminescence using BRC. The pathogen titer (number of pathogenic organisms) in the sample may be determined by photon integration over a time interval, as discussed above.

Example 5

Pathogen Typing by Rolling Circle

Figure 9:
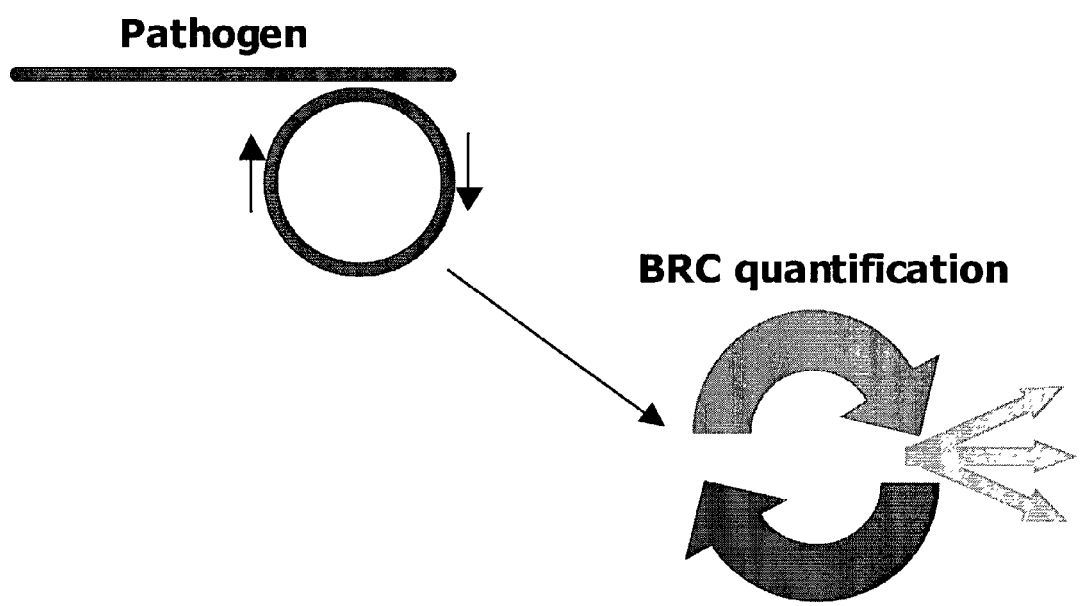
FIG. 9 shows an exemplary embodiment of BRC using a rolling circle technique.

In various embodiments, BRC may be performed using a rolling circle replication process (FIG. 9). In this case, a circular primer sequence is allowed to hybridize with either total RNA or genomic DNA, for example of a pathogen. (Banér et al, *Nucleic Acids Research*, 26:5073–5078, 1998). As discussed above, the primer may be specific for a single type of pathogen, or may react with a family of pathogenic organisms. Alternatively, multiple circular primers specific for different members of a family of pathogens may be used. After hybridization, an exonuclease is added to the solution. The exonuclease digests single-stranded RNA or DNA, leaving intact double stranded RNA or DNA. The double stranded nucleic acid acts as the substrate in a primer extension reaction as discussed above, using reverse transcriptase or DNA polymerase. Formation of PPi is monitored by BRC.

Example 6

Protein-Protein Interaction

Figure 10:
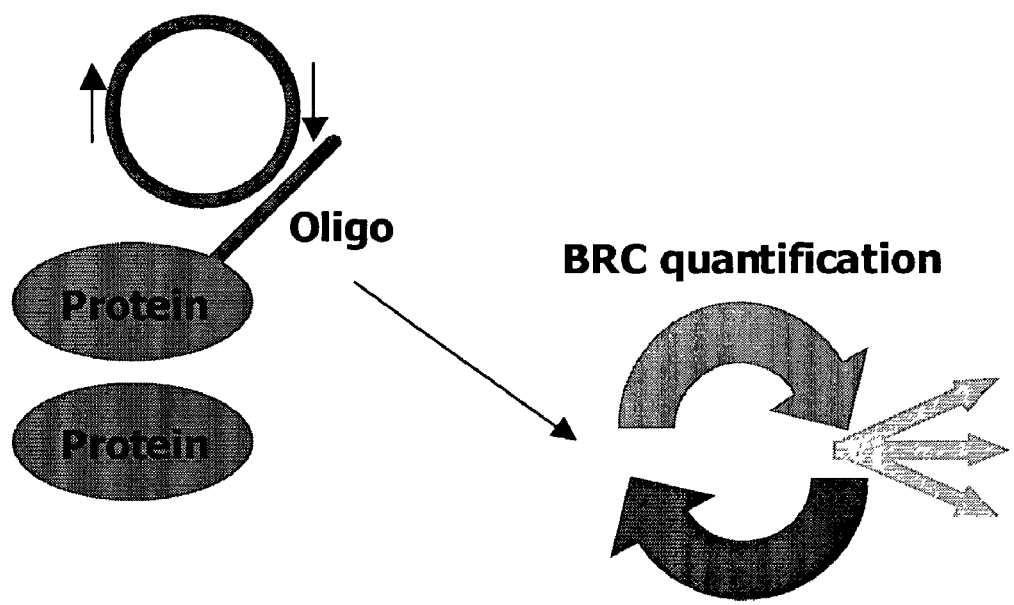
FIG. 10 shows an exemplary embodiment of BRC applied to measurement of protein-protein binding. One protein of the binding pair is labeled with a target oligonucleotide.

In some embodiments, BRC may be used to detect and/or quantify protein-protein binding (FIG. 10). A set of putative target proteins may be immobilized onto a surface, such as a nitrocellulose or nylon membrane or microtiter plate. A protein or peptide that binds to the target protein may be tagged with a short oligonucleotide, for example using a bifunctional cross-linking reagent. The oligonucleotide-tagged protein or peptide may be incubated with the putative target proteins under conditions allowing binding to occur. The remaining unbound proteins may be washed away and the presence of bound oligonucleotide detected by rolling circle reaction as discussed above (Banér et al., 1998), using circular oligonucleotide primers which are complementary to the short oligonucleotide tag. BRC may be used to detect and/or quantify the number of bound target proteins. The skilled artisan will realize that the disclosed method is not limited to protein-protein interactions, but may be applied to any binding pair interaction where one member of the pair may be tagged with a short oligonucleotide. The method may also be applied to arrays of putative target proteins, for example where in vitro translation has been used to create an array of candidate binding proteins from mRNAs.

Example 7

Gene Expression Proriling by Using Total RNA or cDNA

Figure 11:
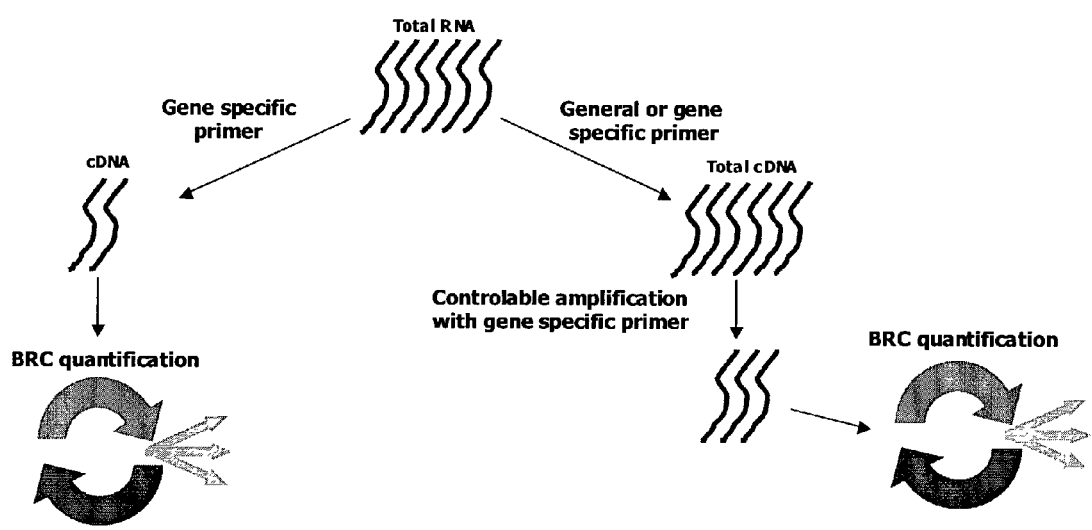
FIG. 11 shows an exemplary embodiment of BRC applied to measurement of gene expression.

Total RNA or cDNA may be incubated with one or more gene specific primers or general primers (FIG. 11). Bound primer/template pairs are extended by reverse transcription or DNA polymerization. Formation of pyrophosphate is detected by BRC, as discussed above, and the amount of target nucleic acid may be quantified. In certain embodiments, a primer is used that is designed to bind specifically to a single gene product (mRNA species), allowing determination of the level of expression for an individual gene. In other embodiments, non-specific primers, such as oligo(dT) and/or random primers may be used. In this case, the mRNA species present in a sample may be first separated, for example by hybridization to a DNA microarray containing complementary sequences for a large number of gene products. Hybridization may be followed by non-specific primer binding, extension and BRC reaction. Alternatively, the oligonucleotides of the array may themselves be used as primers, allowing extension and light emission to occur. In such embodiments, the PPi reaction product may preferably be localized so that light emission is limited to the immediate location of a hybridized target nucleic acid. Many such localization techniques are known in the art, for example using microtiter plates wherein each well contains a probe for an individual gene expression product, or using a commercial apparatus such as a Nanochip® Workstation (Nanogen, San Diego, Calif.).

Example 8

Real Time PCR

There are a variety of applications in which quantification of the amount of PCR reaction products in real time may be desired. The quantification of amplified target in a polymerase chain reaction (PCR) is achieved by incorporation of dNTP. As a result of dNTP incorporation PPi is released. An aliquot of synthesized DNA from each PCR cycle is added to a reaction mixture containing luciferase as disclosed above and thereby one can evaluate/estimate the mass of the molecules for each cycle from the generated light.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

---

What is claimed is:

1. A method comprising:
a) obtaining at least one sample suspected of containing one or more target nucleic acids;
b) generating pyrophosphate (PPi) by replication of the target nucleic acid;
c) adding ATP or PPi to the sample before light is produced, wherein the amount of ATP or PPi is between 0.01 and 10 attomoles;
d) producing light by a bioluminescence regenerative cycle (BRC), wherein the BRC utilizes adenosine 5'-phosphosulphate (APS), ATP sulfurylase, luciferin and luciferase and wherein ATP and PPi reach steady-state concentrations during the bioluminescence regenerative cycle;
e) accumulating the number of photons produced over a time interval; and
f) determining the number of target nucleic acids in the sample.

2. A method comprising:
a) obtaining at least one sample suspected of containing one or more target nucleic acids;
b) generating pyrophosphate (PPi) by replication of the target nucleic acid in the presence of a dATP analog;
c) adding ATP or PPi to the sample before light is produced, wherein the amount of ATP or Ppi is between 0.01 and 10 attomoles;
d) producing light by a bioluminescence regenerative cycle;
e) accumulating the number of photons produced over a time interval; and
f) determining the number of target nucleic acids in the sample.

3. A method of pathogen profiling comprising:
a) obtaining at least one sample containing pathogens;
b) hybridizing a multiplicity of primers to nucleic acids from the pathogens;
c) generating pyrophosphate (PPi) by replication of the nucleic acids in the presence of a dATP analog;
d) adding ATP or PPi to the sample before light is produced, wherein the amount of ATP or PPi is between 0.01 and 10 attomoles;
e) producing light by a bioluminescence regenerative cycle; and
f) detecting the pathogens by the light production.

4. A method comprising:
a) obtaining at least one sample suspected of containing one or more messenger RNAs (mRNAs);
b) adding primers for one or more target mRNAs;
c) generating pyrophosphate (PPi) by replication of one or more target RNAs in the presence of a dATP analog;
d) adding ATP or PPi to the sample before light is produced, wherein the amount of ATP or PPi is between 0.01 and 10 attomoles;
e) producing light by a bioluminescence regenerative cycle;
f) accumulating the number of photons produced over a time interval; and
g) determining the expression level of each target mRNA in the sample.

5. The method of claim 1 wherein said step of adding ATP or PPi comprises adding purified ATP or PPi.

6. The method of claim 4 wherein said step of adding ATP or PPi comprises adding purified ATP or PPi.

* * * * *